United States Patent
Elfar et al.

(10) Patent No.: US 10,695,402 B2
(45) Date of Patent: Jun. 30, 2020

(54) ERYTHROPOIETIN FOR GASTROINTESTINAL DYSFUNCTION

(71) Applicant: University of Rochester, Rochester, NY (US)

(72) Inventors: John Elfar, Rochester, NY (US); Walaa Elfar, Rochester, NY (US); Mark Noble, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 51 days.

(21) Appl. No.: 15/923,275

(22) Filed: Mar. 16, 2018

(65) Prior Publication Data
US 2018/0264083 A1    Sep. 20, 2018

Related U.S. Application Data

(60) Provisional application No. 62/472,278, filed on Mar. 16, 2017.

(51) Int. Cl.
*A61K 38/18* (2006.01)
*A61K 47/60* (2017.01)
*A61K 9/00* (2006.01)
*A61P 1/14* (2006.01)

(52) U.S. Cl.
CPC ........ *A61K 38/1816* (2013.01); *A61K 9/0019* (2013.01); *A61K 47/60* (2017.08); *A61P 1/14* (2018.01)

(58) Field of Classification Search
CPC .. A61K 38/1816; A61K 47/60; A61K 9/0019; A61P 1/14
See application file for complete search history.

(56) References Cited

U.S. PATENT DOCUMENTS

| | | | |
|---|---|---|---|
| 8,933,030 B2 | 1/2015 | Fretzen et al. | |
| 2008/0070975 A1* | 3/2008 | Shah | A61K 9/0019 514/438 |
| 2008/0227685 A1 | 9/2008 | Currie et al. | |
| 2009/0209455 A1 | 8/2009 | Xu et al. | |
| 2009/0258821 A1* | 10/2009 | Cerami | A61K 38/1816 514/1.1 |
| 2011/0118195 A1 | 5/2011 | Currie et al. | |
| 2011/0195046 A1 | 8/2011 | Sigounas et al. | |
| 2012/0053121 A1 | 3/2012 | Besner et al. | |
| 2013/0130984 A1 | 5/2013 | Besner | |
| 2016/0038419 A1 | 2/2016 | Elfar et al. | |
| 2017/0008941 A1 | 1/2017 | Falkenstein et al. | |
| 2017/0027970 A1 | 2/2017 | Wu et al. | |
| 2017/0029481 A1 | 2/2017 | Geysen et al. | |
| 2017/0196851 A1* | 7/2017 | Thottathil | A61K 31/485 |

FOREIGN PATENT DOCUMENTS

WO    2010144865 A2    12/2010

OTHER PUBLICATIONS

Nagib (Intestinal motility in acute uremia and effects of erythropoietin, Saudi Med J 2012, vol. 33) (Year: 2012).*
Guo (Effect of Intraamniotic Dexamethasone Administration on Intestinal Absorption in a Rabbit Gastroschisis Model, Journal of Pediatric Surgery 1995, 30:983-987) (Year: 1995).*
Risby (High mortality among children with gastroschisis after the neonatal period: A long-term follow-up study, Journal of Pediatric Surgery 2017, 52: 431-436) (Year: 2017).*
Ozdamar (Erythropoietin restores bowel damage and hypoperistalsis in gastroschisis, Journal of Pediatric Surgery 2006, 41: 352-357, of record) (Year: 2006).*
Abdullah (Gastroschisis in the United States 1988-2003: analysis and risk categorization of 4344 patients, Journal of Perinatology 2007, 27: 50-55) (Year: 2007).*
Brines (Erythropoietin crosses the blood-brain barrier to protect against experimental brain injury, PNAS 2000, 97 (Year: 2000).*
Nagib et al., "Intestinal motility in acute uremia and effects of erythropoietin," Saudi Med. J. (2012); 33(5):500-507.

* cited by examiner

*Primary Examiner* — Marcela M Cordero Garcia
(74) *Attorney, Agent, or Firm* — Fox Rothschild LLP

(57) ABSTRACT

This invention relates to treating gastrointestinal dysfunction with erythropoietin (EPO) or its analog.

19 Claims, 5 Drawing Sheets

Specification includes a Sequence Listing.

SEQUENCE LISTING

```
<160> NUMBER OF SEQ ID NOS: 4

<210> SEQ ID NO 1
<211> LENGTH: 193
<212> TYPE: PRT
<213> ORGANISM: Homo sapiens

<400> SEQUENCE: 1

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
```

```
            1               5                  10                 15
Leu Glu Ala Lys Glu Ala Glu Asn Ile Thr Thr Gly Cys Ala Glu His
                20                  25                 30

Cys Ser Leu Asn Glu Asn Ile Thr Val Pro Asp Thr Lys Val Asn Phe
                35                  40                 45

Tyr Ala Trp Lys Arg Met Glu Val Gly Gln Gln Ala Val Glu Val Trp
                50                  55                 60

Gln Gly Leu Ala Leu Leu Ser Glu Ala Val Leu Arg Gly Gln Ala Leu
 65                 70                  75                 80

Leu Val Asn Ser Ser Gln Pro Trp Glu Pro Leu Gln Leu His Val Asp
                85                  90                 95

Lys Ala Val Ser Gly Leu Arg Ser Leu Thr Thr Leu Leu Arg Ala Leu
               100                 105                110

Gly Ala Gln Lys Glu Ala Ile Ser Pro Pro Asp Ala Ala Ser Ala Ala
               115                 120                125

Pro Leu Arg Thr Ile Thr Ala Asp Thr Phe Arg Lys Leu Phe Arg Val
               130                 135                140

Tyr Ser Asn Phe Leu Arg Gly Lys Leu Lys Leu Tyr Thr Gly Glu Ala
145                150                 155                160

Cys Arg Thr Gly Asp Arg
               165

<210> SEQ ID NO 3
<211> LENGTH: 193
<212> TYPE: PRT
<213> ORGANISM: Homo sapiens

<400> SEQUENCE: 3

Met Gly Val His Glu Cys Pro Ala Trp Leu Trp Leu Leu Leu Ser Leu
 1               5                  10                 15

Leu Ser Leu Pro Leu Gly Leu Pro Val Leu Gly Ala Pro Pro Arg Leu
                20                  25                 30

Ile Cys Asp Ser Arg Val Leu Gln Arg Tyr Leu Leu Glu Ala Lys Glu
                35                  40                 45

Ala Glu Asn Ile Thr Thr Gly Cys Ala Glu His Cys Ser Leu Asn Glu
                50                  55                 60

Asn Ile Thr Val Pro Asp Thr Lys Val Asn Phe Tyr Ala Trp Lys Arg
 65                 70                  75                 80

Met Glu Val Gly Gln Gln Ala Val Glu Val Trp Gln Gly Leu Ala Leu
                85                  90                 95

Leu Ser Glu Ala Val Leu Arg Gly Gln Ala Leu Leu Val Asn Ser Ser
               100                 105                110

Gln Pro Trp Glu Pro Leu Gln Leu His Val Asp Lys Ala Val Ser Gly
               115                 120                125

Leu Arg Ser Leu Thr Thr Leu Leu Arg Ala Leu Gly Ala Gln Lys Glu
               130                 135                140

Ala Ile Ser Pro Pro Asp Ala Ala Ser Ala Ala Pro Leu Arg Thr Ile
145                150                 155                160

Thr Ala Asp Thr Phe Arg Lys Leu Phe Arg Val Tyr Ser Asn Phe Leu
               165                 170                175

Arg Gly Lys Leu Lys Leu Tyr Thr Gly Glu Ala Cys Arg Thr Gly Asp
               180                 185                190

Arg
```

```
<210> SEQ ID NO 4
<211> LENGTH: 166
<212> TYPE: PRT
<213> ORGANISM: Homo sapiens

<400> SEQUENCE: 4

Ala Pro Pro Arg Leu Ile Cys Asp Ser Arg Val Leu Gln Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

ERYTHROPOIETIN FOR GASTROINTESTINAL DYSFUNCTION

CROSS REFERENCE TO RELATED APPLICATION

This application claims priority to U.S. Provisional Application No. 62/472,278 filed on Mar. 16, 2017. The content of the application is incorporated herein by reference in its entirety.

GOVERNMENT INTERESTS

This invention was made with Government Support under AR060164 awarded by the National Institutes of Health and W81XWH-16-1-0725 awarded by the Department of Defense. The Government has certain rights in the invention.

FIELD OF THE INVENTION

This invention relates to treating gastrointestinal dysfunction with erythropoietin (EPO) or its analog.

BACKGROUND OF THE INVENTION

Gastrointestinal dysfunction, such as intestinal dysmotility, is a frequent and occasionally dominating symptom of various conditions. Intestinal motility is critical to nutrition and several biological functions. Notably, intestinal dysmotility could be both a cause and a result of several disease processes. For example, in the setting of surgical manipulation of the gut, a known ileus results in dysmotility. Inflammatory bowel disease, peritonitis, and even several forms of shock can also lead to dysmotility. Independent of cause, the loss of normal gut function compromises nutrition and survival. Several motility agents are currently used in humans but without well-defined mechanistic detail. There is a need for novel therapeutic agents and treatment methods.

SUMMARY OF INVENTION

This invention relates to treating gastrointestinal dysfunction with EPO or its analog.

In one aspect, the invention features a method for increasing intestinal motility in a subject in need thereof, The method comprises administering to the subject an effective amount of erythropoietin or an analog thereof.

The subject can be one suffering from a condition selected from the group consisting of an intestinal injury, an abdominal trauma, an intestinal inflammatory condition, an intestinal infection, slow transit constipation, post-operative ileus, a neurodegenerative injury, a neurotraumatic injury, a congenital problem, and a malnutrition-malabsorption problem. The malnutrition-malabsorption problem can be caused by one or more selected from the group consisting of an intestinal injury, an abdominal trauma, an intestinal inflammatory condition, an intestinal infection, constipation (e.g., constipation caused by opiate use), post-operative ileus, a neurodegenerative injury, a neurotraumatic injury, a congenital problem, Gaucher disease, refeeding syndrome, extremely low birth weight infants, cancer cachexia, infection, cancer, spinal cord dysfunction, spinal dysraphism, bifida, tumor, central nervous system dysfunction, peripheral neuropathy, removal part of the gastrointestinal tract, hemorrhage, liver dysfunction, celiac disease, cystic fibrosis, muscular dystrophies, and cerebral palsy. Examples of the congenital problem include Gastroschisis, omphalocele, aganglionic megacolon, Hirschprung's disease, chronic intestinal pseudo-obstruction, small left colon syndrome, anorectal anomalies, esophageal dysplasia and atresias, ectopic anus, congenital hernias, and internal anal sphincter achalasia. In some embodiments, the condition is an intestinal inflammatory condition and the subject does not have anemia. In some embodiments, the subject does not have acute uremia due to kidney failure. The subject can be a mammal, such as a human and a non-human mammal.

In the method described above, the EPO or analog can be administered as a conjugate, such as a PEGylated version of the erythropoietin or analog thereof. The EPO or analog thereof can be administered at 100 to 1,000 U/kg, e.g., 200-500 U/Kg, 250-350 U/kg, or about 300 U/kg. The EPO or the analog can be administered via any suitable routes known in the art, e.g., orally, insertion, implantation or injection (such as subcutaneous injection or intravenous injection). For treating gastrointestinal dysfunction (e.g., such as intestinal dysmotility), erythropoietin or the analog can be administered to the subject over a treatment period of least 24 hours, e.g., 24 hours, 2, 3, 4, 5, 6, 7, 8, 9, or 10 days (e.g., 1-10 days, 2-8 days, and 3-7 days), or 1, 2, 3, or 4 weeks, or 1, 2, 3, 4, 5, 6, 7, 8, 9, 11, or 12 months or even years for prolonged treatment.

In another aspect, the invention provides a use of an erythropoietin or an analog thereof in the manufacture of a medicament for increasing intestinal motility.

The details of one or more embodiments of the invention are set forth in the description below. Other features, objectives, and advantages of the invention will be apparent from the description and from the claims.

DETAILED DESCRIPTION OF THE INVENTION

Figure 1A:
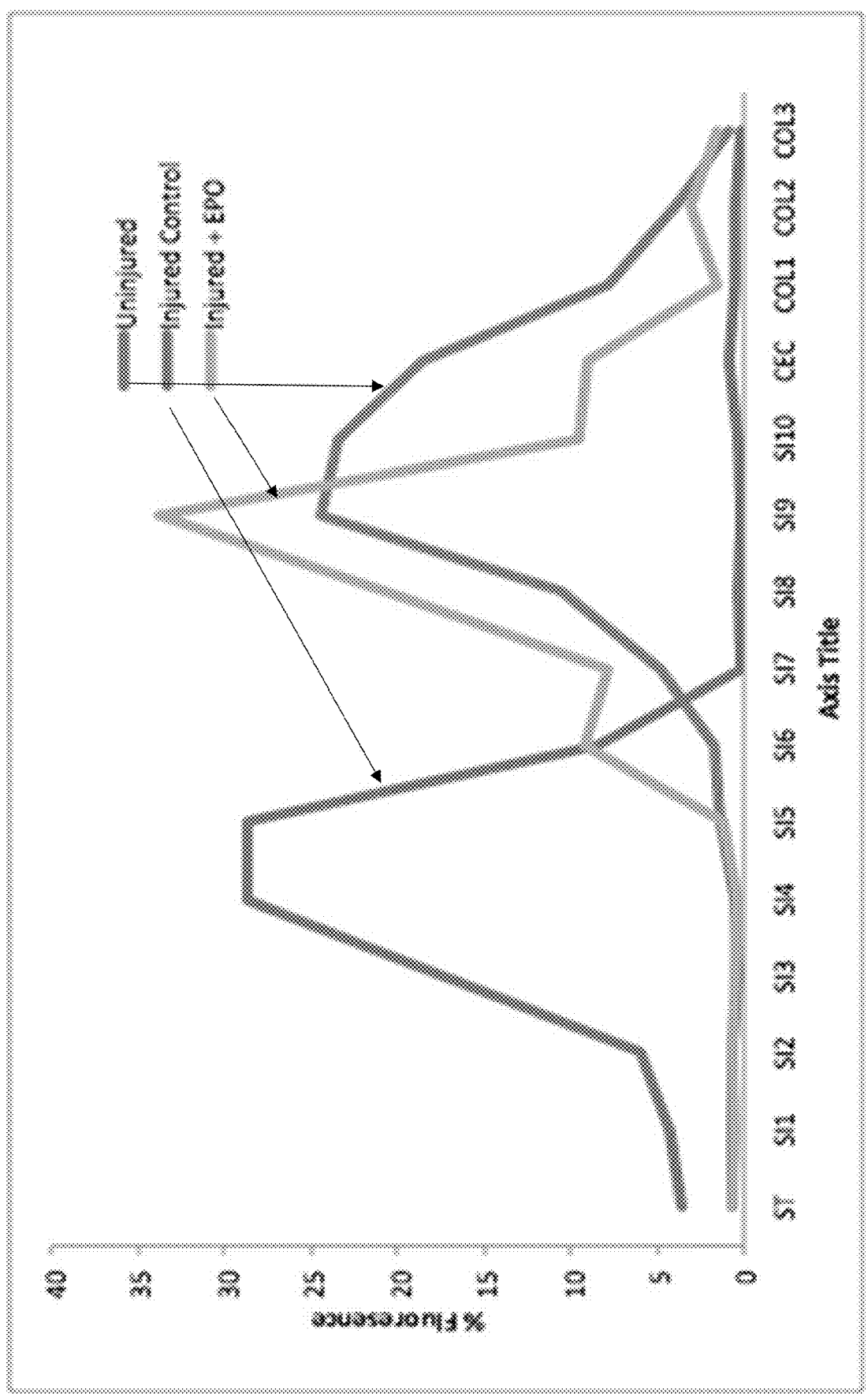
FIG. 1A is a diagram showing intestinal transit through the gastrointestinal tract from the stomach (ST) through ten segments of small intestine (SI1-10) and cecum (CEC) through colon (COL1-3) (n=6 per group).

This invention is based, at least in part, on an unexpected discovery that erythropoietin (EPO), a hormone approved for use in the treatment of anemia, has effects on multiple tissue types and organ systems. In particular, as disclosed herein, it was found that EPO unexpectedly accelerated functional recovery of gastrointestinal dysmotility via EPO receptors on Schwann cells. Accordingly, this invention provides methods using EPO or its analogs in treating gastrointestinal dysmotility.

Gastrointestinal Dysmotility

As mentioned above, gastrointestinal dysmotility is a frequent and occasionally dominating symptom of various conditions. Although the primary cause of dysmotility is abdominal trauma, several disease processes have dysmotility as their common effect. For example, inflammation in the gut is a common cause of dysmotility (e.g., inflammatory bowel diseases (IBD), such as Chron's Disease, and Ulcerative Colitis). Systemic bacterial infections which result in bacteremia and sepsis can also cause dysmotility as do localized collections such as peritonitis and ascites. Also, several forms of neurodegenerative and neurotraumatic injuries result in dysmotility as in the case of spinal cord injury patients who have autonomic dysfunction.

Whether or not dysmotility is the result of a primary gut process or a secondary effect of another systemic disease or injury process, the results affect nutrition. Different parts of the gastrointestinal system are responsible for the absorption of different nutrients. Stasis in one segment or slowing over the entire gut can be life threatening.

The intestinal glial cells (IGCs) are constituents of the enteric nervous system which may play a role in the regulation of inflammatory processes and motility in the gut. IGCs show remarkable similarities to glial cells elsewhere in the body and promotility functions which may possibly correlate with their functions in facilitating peripheral nerve impulse conduction. Functional recovery improves in peripheral nerve injury (resulting from a crush injury to a nerve, including neurons and glia) after EPO administration and that this improvement is significantly related to improvements in glial cell function and resistance to oxidative stress. EPO improves the myelination, neuron and glial cell counts, functional recovery, and even in-vitro metrics of glial-cell function.

A key factor in the development of dysmotility involves localized tissue inflammation from oxidative stress. Tissue expression of nitric oxide is known to be a common pathway resulting in dysmotility from several causes. Interestingly, it has been found that erythropoietin to be protective against the effects of oxidative stress on neurons and Schwann cells in vitro and to speed functional recovery in animals with peripheral nervous system injuries.

Agents that promote gastrointestinal motility are sparse. To date, no direct studies have implicated erythropoietic hormones as a primary means of promoting motility. Some agents currently in use focus on promotility actions in one anatomic area as is the known activity of erythromycin and metoclopramide on the stomach. Augmentin is believed to accelerate motility in the small bowel and docusate sodium promotes motility chiefly through actions as a laxative in the large bowel. None of these agents has a fully described mechanism of action, though docusate is believed to soften stools, allowing more facilitated passage. The pathophysiology of dysmotility disorders is likely anatomically diverse (as are the points of action of these diverse agents). To inventors' knowledge, no work has delved into the question of EPO for dysmotility where the cause is not a lack of EPO per se. To date, no direct studies have implicated erythropoietic hormone as a primary means of promoting motility in the presence of normal renal function.

As disclosed herein, EPO could serve as a promotility agent in the only standard model of dysmotility in wild-type rodents which results from an injury correlating with a human disease process. See instance, as described in the examples section below, the intestinal manipulation model in rodents, where animals underwent a surgical ileus-inducing procedure, were used to test EPO for its ability as a promotility agent.

It was found that wild type mice which underwent intestinal manipulation showed significant slowing of their intestinal transit compared with sham-manipulated controls. In contrast, the EPO treated counterparts were indistinguishable from a functional standpoint when compared with sham-injured wild type animals. It was also found that mice selectively deficient in the expression the receptor for EPO (EPO-R) on Schwann cells showed significant slowing of their intestinal transit compared with sham-injured EPO-R deficient counterparts. However, EPO treatment did not restore normal transit time in these animals and had no functional effect.

As also disclosed herein, EPO treatment prevents intestinal dysmotility in a manner which may depend on expression of EPO-R in Schwann cells. The magnitude of this effect is large enough to render treated animals which would suffer dysmotility indistinguishable from sham-injured animals when treatment with EPO is provided. This effect bears relevance in the treatment of primary dysmotility and also dysmotility from secondary causes.

Erythropoietin

Erythropoietin, a glycoprotein produced in the kidney, is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, Ann. Rev. Med. 29:51 (1978); Eschbach and Adamson, Kidney Intl. 28:1 (1985). Recombinant human erythropoietin (rHuEpo or epoetin alfa) is commercially available as Epogen™ (Amgen Inc., Thousand Oaks, Calif.) and as Procrit™ (Ortho Biotech Inc., Raritan, N.J.). EPO is frequently used to increase the hematocrit of cancer patients who become anemic because of their disease or because of treatment with chemotherapeutic drugs. EPO is indicated for treatment of anemia, including anemias associated with cancer chemotherapy, chronic renal failure, malignancies, adult and juvenile rheumatoid arthritis, disorders of haemoglobin synthesis, prematurity, and zidovudine treatment of HIV infection. US20110195046. EPO is known to alter recovery after several insults to the nervous system. See, e.g., US20160038419. All of these documents are incorporated by reference in their entirety.

Although EPO is known to stimulate erythrogenesis and alter recovery after several insults to the nervous system, the inventors found no reports in the literature to establish a use of EPO in the treatment of primary or secondary gastrointestinal dysmotility. As disclosed herein, it was unexpectedly found that EPO accelerated functional recovery in a standard rodent model of gastrointestinal dysmotility. As shown in the examples below, mice were subjected to intestinal manipulation as a means to induce standard functional dysmotility in a standardized model. Wild-type animals were compared to those selectively deficient in the expression of the receptor for erythropoietin on Schwann Cells. All animals underwent standard functional measures of colonic transit and, after sacrifice, standard immunohistochemical and histomorphometric analyses of harvested tissues per approved institutional protocols.

Accordingly, EPO and its analogs can be used as therapeutic agents in treatment of gastrointestinal dysmotility. Examples of the therapeutic agents can include EPO analogs, EPO isoforms, EPO mimetics, EPO fragments, hybrid EPO proteins, fusion proteins oligomers and multimers of the above, homologues of the above, including receptor blockers or agonists, glycosylation pattern variants of the above, and mutants of the above, regardless of the method of synthesis or manufacture thereof including but not limited to, recombinant vector expression whether produced from cDNA or genomic DNA, synthetic, transgenic, and gene activated methods.

Shown below is the amino acid sequence of a protein variant encoded by human EPO gene, which corresponds to Genbank Accession No. NP_000790.2 (SEQ ID NO: 1), where amino acid residue 1-27 is the signal peptide and amino acid residues 28-193 (underlined, SEQ ID NO: 2) is the sequence of human EPO.

```
MGVHECPAWL WLLLSLLSLP LGLPVLGAPP RLICDSRVLE

RYLLEAKEAE NITTGCAEHC SLNENITVPD TKVNFYAWKR

MEVGQQAVEV WQGLALLSEA VLRGQALLVN SSQPWEPLQL

HVDKAVSGLR SLTTLLRALG AQKEAISPPD AASAAPLRTI

TADTFRKLFR VYSNFLRGKL KLYTGEACRT GDR
```

Shown below is the amino acid sequence of another protein variant encoded by human EPO gene, which corresponds to Genbank Accession No. CAA26095 (SEQ ID NO: 3), where amino acid residue 1-27 is the signal peptide and amino acid residues 28-193 (underlined, SEQ ID NO: 4) is the sequence of human EPO. The different residues in these two variants are in bold.

```
MGVHECPAWL WLLLSLLSLP LGLPVLGAPP RLICDSRVLQ

RYLLEAKEAE NITTGCAEHC

SLNENITVPD TKVNFYAWKR MEVGQQAVEV WQGLALLSEA

VLRGQALLVN SSQPWEPLQL

HVDKAVSGLR SLTTLLRALG AQKEAISPPD AASAAPLRTI

TADTFRKLFR VYSNFLRGKL

KLYTGEACRT GDR
```

The term "erythropoietin" and its abbreviation "EPO" refer to a protein having the amino acid sequence of SEQ ID NO: 1, 2, 3, or 4, or a protein or polypeptide substantially homologous thereto, whose biological properties relate to the stimulation of red blood cell production and the stimulation of the division and differentiation of committed erythroid progenitors in the bone marrow. Both the naturally occurring human erythropoietin glycoprotein as well as recombinant human erythropoietin (e.g., rHuEpo or epoetin alfa, available commercially as EPOGEN. (Amgen Inc., Thousand Oaks, Calif.) and as PROCRIT (Ortho Biotech Inc., Raritan, N.J.)) can be used in this invention. The term "EPO" or "erythropoietin" also covers chemically modified EPO. Examples of chemically modified EPO include EPO subjected to conformational change, addition or deletion of a sugar chain, and EPO to which a compound such as polyethylene glycol has been bound. Once purified and tested by standard methods or according to the method described in the examples below, EPO can be included in a pharmaceutical composition.

Recombinant erythropoietin may be prepared via expression in eukaryotic cells, for example in CHO cells, or BHK cells, or HeLa cells by recombinant DNA technology or by endogenous gene activation, i.e. the erythropoietin glycoprotein is expressed by endogenous gene activation, see for example U.S. Pat. Nos. 5,733,761, 5,641,670, 5,733,746, WO 93/09222, WO 94/12650, WO 95/31560, WO 90/11354, WO 91/06667, and WO 91/09955.

In one embodiment the erythropoietin is human EPO. In one embodiment the human erythropoietin has the amino acid sequence set out in SEQ ID NO: 1, 2, 3, or 4. In one embodiment the human erythropoietin has the amino acid sequence set out in SEQ ID NO: 2 or 4. The term "erythropoietin" also denotes variants of the protein of SEQ ID NO: 1 or of SEQ ID NO: 2, in which one or more amino acid residues have been changed, deleted, or inserted, and which has comparable biological activity as the not modified protein, such as those reported in, e.g., EP 1 064 951 or U.S. Pat. No. 6,583,272. A variant may have the amino acid sequence of human erythropoietin having from 1 to 6 additional sites for glycosylation. The specific activity of erythropoietin can be determined by various assays known in the art. The biological activity of the purified erythropoietin are such that administration of the protein by injection to human patients results in bone marrow cells increasing production of reticulocytes and red blood cells compared to non-injected or control groups of subjects. The biological activity of the erythropoietin obtained and purified in accordance with the method as reported herein can be tested by methods according to Bristow, A., Pharmeuropa Spec. Issue Biologicals BRP Erythropoietin Bio 97-2 (1997) 31-48.

Amino acid sequence variants of erythropoietin can be prepared by introducing appropriate modifications into the nucleotide sequence encoding the erythropoietin, or by peptide synthesis. Such modifications include, for example, deletions from, and/or insertions into, and/or substitutions of residues within the amino acid sequences of the erythropoietin. Any combination of deletion, insertion, and substitution can be made to arrive at the final construct, provided that the final construct possesses comparable biological activity to the human erythropoietin.

As used herein, the term "conservative sequence modifications" refers to amino acid modifications that do not significantly affect or alter the EPO-R binding characteristics of the EPO containing the amino acid sequence. Conservative amino acid substitutions are ones in which the amino acid residue is replaced with an amino acid residue having a similar side chain. Families of amino acid residues having similar side chains have been defined in the art.

Amino acid substitutions can be made, in some cases, by selecting substitutions that do not differ significantly in their effect on maintaining (a) the structure of the peptide backbone in the area of the substitution, (b) the charge or hydrophobicity of the molecule at the target sit; or (c) the bulk of the side chain. For example, naturally occurring residues can be divided into groups based on side-chain properties; (1) hydrophobic amino acids (norleucine, methionine, alanine, valine, leucine, and isoleucine); (2) neutral hydrophilic amino acids (cysteine, serine, threonine, asparagine, and glutamine); (3) acidic amino acids (aspartic acid and glutamic acid); (4) basic amino acids (histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Examples of substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. Exemplary substitutions are shown in Table 1. Amino acid substitutions may be introduced into human erythropoietin and the products screened for retention of the biological activity of human erythropoietin.

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

While many EPO preparations can be used, highly purified EPO is preferred. Examples of EPO and its analog include mammalian EPO (e.g., human EPO) or EPO having substantially the same biological activity as mammalian EPO. All of naturally occurring EPO, genetic engineered EPO, and chemically synthesized EPO can be used. EPO obtained by recombinant DNA technology may have the same amino acid sequence as naturally a occurring EPO (SEQ ID NO: 1, 2, 3 or 4) or an functionally equivalent thereof.

EPO Analogs

As used herein an analog of EPO refers to a protein or non-protein molecule that has a similar three-dimensional structure to human EPO and is able to mimic the interaction of EPO with the EPO receptor. Examples include peptide analogs of EPO.

As used herein, peptide analogs are those compounds which, while not having amino acid sequences identical to that of EPO, have a similar three-dimensional structure. In protein molecules which interact with a receptor, the interaction takes place at the surface-accessible sites in a stable three-dimensional molecule. By arranging the critical binding site residues in an appropriate conformation, peptides which mimic the essential surface features of EPO binding regions may be designed and synthesized in accordance with known techniques. A molecule which has a surface region with essentially the same molecular topology to the binding surface of EPO will be able to mimic the interaction of EPO with the EPO receptor. Methods for determining peptide three-dimensional structure and analogs thereto are known, and are sometimes called "rational drug design techniques." See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock. All of these U.S. patents are incorporated by reference in their entirety.

Peptides which mimic the biological activity of erythropoietin (EPO receptor ligands or EPO receptor agonist) may be substituted for EPO in the methods of the present invention. The sequence of such peptides may represent fragments of the full-length EPO protein sequence, which fragments are capable of binding to and activating the EPO receptor. Additionally, peptides with sequences dissimilar to that of EPO may be utilized in the methods of the present invention, where such peptides mimic the biological activity of EPO. Wrighton et al. report the identification and characterization of small peptides that bind to and activate the erythropoietin receptor on the surface of target cells, although the peptides' sequences are not similar to the primary sequence of EPO (Wrighton et al., Science 273:458 (26 Jul. 1996)). These peptide agonists are represented by a 14-amino acid disulfide-bonded cyclic peptide with an identified minimum consensus sequence. The structure of a complex of one such peptide mimetic with the erythropoietin receptor is described by Livnah et al., Science 273:464 (26 Jul. 1996).

Additional peptide analogs that bind to the EPO receptor have been described in U.S. Pat. Nos. 7,084,245; 7,414,105; and 7,459,522, US 20170008941, US 20110195046, US 20170029481, US20090209455, US20160038419, and US20170027970, each of which are incorporated herein by reference. An X-ray crystal structure of a peptide agonist complexed with the extracellular domain of the EPO receptor has also been published. See Livnah et al., Science, 273, 1996, 464-471; the crystal structure coordinates are hereby incorporated by reference.

The EPO or it analog used in accordance with the invention can be modified, for example, to increase the half-life, efficacy, metabolism, and/or potency of the protein using methods known in the art. For example, an EPO molecule or it analog can be linked to polyethylene glycol ("PEG").

Polyethylene glycol is a polyalkylene glycol compound or a derivative thereof, with or without coupling agents or derivatization with coupling or activating moieties (e.g., with thiol, triflate, tresylate, azirdine, oxirane or preferably with a maleimide moiety). Compounds such as maleimido monomethoxy PEG are exemplary of activated PEG compounds. Other polyalkylene glycol compounds, such as polypropylene glycol, may be used in accordance with the present invention. Other appropriate polymer conjugates include, but are not limited to, non-polypeptide polymers, charged or neutral polymers of the following types: dextran, colominic acids or other carbohydrate based polymers, biotin derivatives and dendrimers, for example.

The PEG can be linked to an amino acid residue such as lysine, histidine, tryptophan, aspartic acid, glutamic acid and cysteine, for example, or other such amino acids (or mimetics thereof) known to those of skill in the art. The PEG moiety, or moieties, attached to the molecule may range in molecular weight from about 200 to about 20,000 MW. In some embodiments, the PEG moiety will be from about 1,000 to 8,000 MW, from about 3,250 to 5,000 MW, or about 5,000 MW. In certain embodiments, the total molecular weight of the PEG moieties on the molecule may range from 10,000 to 50,000 MW, and may preferably be over about 30,000 MW. In some embodiments, the total molecular weight of the PEG moieties on the EPO or EPO analog the invention is such that renal filtration of the compound is precluded, and in such embodiments renal clearance of the compound may be substantially reduced, such as by about ½ or less, by about ⅓ or less, by about ⅕ or less, or by about ¹⁄₁₀ or less, as compared to a corresponding unpegylated molecule.

The number of PEG molecules covalently bound per molecule of the invention may vary depending upon the desired stability (i.e., serum half-life), but in certain embodiments, is one, two or three PEG molecules. EPO molecules disclosed herein can be linked to PEG molecules using techniques shown in, but not limited to, U.S. Pat. Nos. 4,179,337; 5,382,657; 5,972,885; 6,177,087; 6,165,509; 5,766,897; and 6,217,869, each of which are incorporated herein by reference.

In other embodiments, other moieties may be attached to EPO or its analog of the invention to extend serum half-life of the EPO or analog. For instance, human serum albumin, transferrin, Ig segments or other serum proteins may be attached, linked or conjugated to EPO or its analog. Such molecules and methods of attachment are known in the art and are described, e.g., in U.S. Pat. Nos. 7,238,667; 7,176,278; and 5,766,883, each of which is incorporated herein by reference. Additional moieties that may be used to extend the half-life of the EPO or its analog of the present invention can be found US20170029481 and US20170008941, which are incorporated herein by reference.

The EPO or its analog described herein may employ various natural or non-natural amino acids, i.e., amino acids other than the standard, genetically-encoded amino acids, and/or may employ amino acid mimetics, such as substitute replacements of moieties in the peptide backbone, all of which are described US20170029481 and US20170008941, which are incorporated herein by reference.

Pharmaceutical Compositions

The EPO, EPO conjugate, and EPO analog described herein are useful for preparation of pharmaceutical compositions for increasing intestinal motility in a subject in need thereof. The pharmaceutical compositions can be provided wherein the EPO, EPO conjugate, or an analog thereof, alone or in combination, can be combined with any pharmaceutically acceptable carrier or medium. In some embodiments, the pharmaceutical composition comprises a peptide (or its conjugate or analog) or pharmaceutically acceptable salt thereof as described herein. The pharmaceutical composition may comprise two or more peptides/analog thereof or pharmaceutically acceptable salts thereof described herein.

The active compounds described above may be formulated for administration in a pharmaceutical carrier in accordance with known techniques. See, e.g., Remington, The Science And Practice of Pharmacy (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy consisting essentially of admixing the components, optionally including one or more accessory ingredients.

Pharmaceutical compositions according to the present invention may be formulated for administration by inhalation (via mouth or nose), oral, parenteral, transdermal or transmucosal means; parenteral modes of administration are preferred. In general, pharmaceutical compositions according to the present invention may comprise effective amounts of an EPO, an EPO conjugate or an analog thereof according to the present invention (or derivative products thereof) together with pharmaceutically acceptable excipients, diluents, preservatives, solubilizers, emulsifiers, adjuvants and/or carriers. Such compositions can include diluents of various buffer content (e.g., Tris-HCl, acetate, phosphate), pH and ionic strength; additives such as detergents and solubilizing agents (e.g., Tween 20, Tween 80, Polysorbate 80), anti-oxidants (e.g., ascorbic acid, sodium metabisulfite), preservatives (e.g., thimersol, benzyl alcohol) and bulking substances (e.g., lactose, mannitol). Such compositions may influence the physical state, stability, rate of in vivo release and rate of in vivo clearance of the EPO, EPO conjugate, or analog. The pharmaceutical composition according to the present invention may be prepared in liquid form or may be in dried powder (e.g., lyophilized) form.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

The compositions described herein may be administered systemically or locally by any suitable means known in the art, e.g.: orally (e.g., using capsules, powders, solutions, suspensions, tablets, sublingual tablets and the like), by inhalation (e.g., with an aerosol, gas, inhaler, nebulizer or the like), to the ear (e.g., using ear drops), topically (e.g., using creams, gels, liniments, lotions, ointments, pastes, transdermal patches, etc), ophthalmically, rectally (e.g., using enemas or suppositories), nasally, buccally, vaginally (e.g., using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

For treatment of gastrointestinal disorders, the EPO, EPO conjugate, or an analog thereof described herein is preferably administered orally, e.g., as a tablet, capsule, sachet containing a predetermined amount of the active ingredient pellet, gel, paste, syrup, bolus, electuary, slurry, powder, lyophilized powder, granules, as a solution or a suspension in an aqueous liquid or a non-aqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein.

Preferred methods of administration of EPO, EPO conjugate, or an analog thereof of the present invention may be parenteral (intramuscular, intraperitoneal, intravenous or subcutaneous injection). Preparations according to this invention for parenteral administration include sterile aqueous or non-aqueous solutions, suspensions or emulsions. Examples of non-aqueous solvents or vehicles include propylene glycol, polyethylene glycol, vegetable oils such as olive oil and corn oil, gelatin and injectable organic esters such as ethyl olate. Such dosage forms may also contains adjuvants such as preserving, wetting, emulsifying and dispersing agents. They may be sterilized by, e.g., filtration through a bacteria retaining filter, by incorporating sterilizing agents into the compositions, by irradiating the compositions, or by heating the compositions. They can also be manufactured using sterile water, or some other sterile injectable medium, immediately before use.

Another preferred method of administration is through the use of a micro needle with a pen-style dosing cartridge. Such a delivery would allow a patient to self-treat. A therapeutically effective dose could be contained within about 10-50 µl, such as 20 µl of fluid.

EPO is a U.S. Food and Drug Administration-approved drug for use in the treatment of anemia with a minimal side-effect profile. The dosage and timing of EPO or EPO conjugate (or an analog thereof) administration used depend upon the desired effect. It will be apparent to those skilled in the art how to determine, by routine experimentation, the dosage and timing of EPO, EPO conjugate, or an analog thereof to achieve a desired effect. It also will be understood that the specific dose level and frequency of dosage for any particular patient may be varied and depends upon a variety of factors, including the activity of the specific EPO composition employed, the metabolic stability and length of action of the EPO composition, the age, body weight, general health, sex, diet, mode and time of administration, rate of excretion, drug combination, the severity of the particular condition, and the host undergoing therapy.

As EPO is already used in humans for other indications and has a favorable side-effect profile. For example, doses of up to 1,500 Units/kg for three to four weeks have been administered without toxic effects due to EPO itself. Eschbach et al., in: Prevention of Chronic Uremia (Friedman et al., eds.), Field and Wood Inc., Philadelphia, pp. 148-155 (1989). One of skill in the art on considering the therapeutic context, age and general health of the recipient, will be able to ascertain proper dosing; the selected dosage depends upon the desired therapeutic effect, on the route of administration and on the duration of the treatment desired. Generally, dosage levels of 0.001 to 10 mg/kg of body weight daily are administered to a subject; dosage may be lower for intravenous injection or infusion. The dosing schedule may vary depending on the circulation half-life and the formulation used.

For increasing intestinal motility in a subject in need thereof, suitable dosages may range from about 1, 10, 50, 100, or 200 Units per kilogram (U/kg) to about 400, 450, 500, 600, 700, 800, 900, 1,000, 2000, 5000, or 10,000 U/kg. For example, a suitable dosage can be 100 to 1000, 200 to 500, 250 to 350, about 300 U/kg.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier.

In addition to active agents or their salts, the pharmaceutical compositions may contain other additives, such as pH-adjusting additives. In particular, useful pH-adjusting agents include, but are not limited to, acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include, but are not limited to, methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The EPO, EPO conjugate, or an analog thereof of the present invention may be administered in conjunction with one or more additional active ingredients or pharmaceutical compositions. For example, the EPO, EPO conjugate, or an analog thereof can be co-administered with other agents used to treat gastrointestinal disorders including but not limited to the agents described herein. In another aspect, suitable pharmaceutical compositions may comprise one or more other therapeutic agents. Such therapeutic agents include, without limitation, analgesic agents; anti-secretory agents, including proton pump inhibitors, acid pump antagonists, H2 receptor antagonists; PDE5 inhibitors; GABA-B antagonists; bile acid sequestrants; prokinetic and promotility agents; antidepressants; antibiotics; antiemetics; and mucosal-protecting agents.

Method of Treatment

The present invention also relates to methods of treatment using the EPO, EPO conjugate, or an analog thereof described above for increasing intestinal motility in a subject in need thereof. For example, the present invention provides methods for therapeutic treatment of disorders associated with gastrointestinal dysfunction, such as intestinal dysmotility, which methods comprise administering an EPO, EPO conjugate, or an analog thereof in amounts sufficient to stimulate the EPOR and thus alleviate the symptoms associated with the dysmotility.

Although the method disclosed herein leads to increased level EPO, EPO conjugate, or an analog thereof in a subject, the subject does not have to be deficient in endogenous EPO expression. That is, the subject to be treated can have normal level of endogenous EPO. As the invention disclosed herein is based on EPO's unexpected effects on gastrointestinal dysmotility via EPO receptors, a subject can be treated with the method as long as increasing intestinal motility is needed. In some embodiments, the method can include examining the subject's intestinal motility at one or more of the following points of time: prior to administering EPO, EPO conjugate, or an analog thereof, during the course of the treatment, or after the treatment. The method can include comparing results of the examinations obtained from different points of time. In some embodiments, the method can be used on EPO-deficient patients where the proximate cause of the dysmotility is not known to be uremia per se. In that case, the methods disclosed here are not intended to correct the EPO level itself in the subject but rather for its direct effect on gastrointestinal dysmotility. Thus, the treatment dosing and duration can be lower or shorter than those for treating hematocrit and anemia. To that end, the inventors discovered that EPO, EPO conjugate, or an analog thereof causes very early improvements in dysmotility which preceded effects on hematocrit and anemia. Accordingly, the use of EPO, EPO conjugate, or an analog thereof for dysmotility is distinct from the use to correct other problems such as acute uremia due to, e.g., kidney failure.

As used herein, the term "subject" refers to an animal, preferably a mammal, who has been the object of diagnosis, treatment, observation or experiment. Examples of a subject can be a human, a livestock animal (beef and dairy cattle, sheep, poultry, swine, etc.), or a companion animal (dogs, cats, horses, etc). In some embodiment, the EPO, EPO conjugate, or an analog thereof may be administered to warm blooded animals, preferably mammals, more preferably humans, to simulate the binding of the EPO, EPO conjugate, or an analog thereof to the EPOR in vivo.

As disclosed herein, the subject can be one suffering from a condition that causes gastrointestinal dysfunction such as dysmotility. Such a condition can be a congenital problem or dietary problem. Examples of such a condition include an intestinal injury, an abdominal trauma, an intestinal inflammatory condition, an intestinal infection, slow transit constipation, post-operative ileus, a neurodegenerative injury, a neurotraumatic injury, a congenital problem, and a malnutrition-malabsorption problem.

The malnutrition-malabsorption problem can be caused by one or more selected from the group consisting of an intestinal injury, an abdominal trauma, an intestinal inflammatory condition, an intestinal infection, constipation, post-operative ileus, a neurodegenerative injury, a neurotraumatic injury, a congenital problem, Gaucher disease, refeeding syndrome, extremely low birth weight infants, cancer, cancer cachexia, infection, spinal cord dysfunction, spinal dysraphism, bifida, tumor, central nervous system dysfunction, peripheral neuropathy, removal part of the gastrointestinal tract, hemorrhage, liver dysfunction, celiac disease, cystic fibrosis, muscular dystrophies, and cerebral palsy.

The congenital problem can be one selected from the group consisting of Gastroschisis, omphalocele, aganglionic megacolon, Hirschprung's disease, chronic intestinal pseudo-obstruction, small left colon syndrome, anorectal anomalies, esophageal dysplasia and atresias, ectopic anus, congenital hernias, and internal anal sphincter achalasia.

In some example, the condition is an intestinal inflammatory condition and the subject does not have anemia. In that case and others, the treatment method is not to correct the EPO level itself but rather for treating dysmotility in the manner described herein. For example, the subject does not have acute uremia due to, e.g., kidney failure.

In a further embodiment, the gastrointestinal disorder is constipation. The constipation can be chronic constipation, idiopathic constipation, due to post-operative ileus, or caused by opiate use. Clinically accepted criteria that define constipation include the frequency of bowel movements, the consistency of feces and the ease of bowel movement. One common definition of constipation is less than three bowel movements per week. Other definitions include abnormally hard stools or defecation that requires excessive straining (Schiller 2001, Aliment Pharmacol Ther 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple Sclerosis, Parkinson's disease, spinal cord lesions, Neurofibromatosis, autonomic neuropathy, Chagas disease, Hirschsprung's disease and Cystic fibrosis. Constipation may also be the result of surgery (postoperative ileus) or due to the use of drugs such as analgesics (like opioids), antihypertensives, anticonvulsants, antidepressants, antispasmodics and antipsychotics.

EPO has been clinically used for a variety of purposes including to correct anemia arising from chronic renal failure and cancers in adults. As used herein, methods referring to the use of EPO or erythropoietin include the use of recombinant erythropoietin, synthetic erythropoietin, chemically modified erythropoietin, darbepoieten, glycosylated erythropoietin, EPO-alpha, EPO-beta, EPO-delta, EPO-zeta, and EPO-omega and combinations thereof. Methods of making and using EPO as well as its variants and derivatives are known and described in, for example, U.S.

Pat. Nos. 5,955,422; 5,547,933; 5,441,868; 5,618,698; 5,756,349; and 5,621,080, the contents of each of which are incorporated herein by reference in their entireties. Further, EPO is commercially available from a variety of sources including Amgen (Thousand Oaks, Calif.), Hoffmann-La-Roche (Basel, Switzerland) and Shire Pharmaceuticals Group PLC (St. Helier, Jersey). Optionally, 0.01 U/kg to 5000 U/kg of EPO is administered to the subject.

In addition to erythropoietin polypeptides or peptide analogs thereof, nucleotide sequences encoding the polypeptides or analogs can also be used to practice the invention disclosed herein. Accordingly, in another aspect of the present invention, the EPO can be administered to a subject by forcing the expression of the EPO from a target cell. The EPO that is expressed in the target cell can be an expression product of an EPO gene. The sequence of the gene encoding native human EPO, as well as methods of obtaining the same, are described in, e.g., U.S. Pat. Nos. 4,954,437 and 4,703,008, incorporated herein by reference in their entirety, as well as in Jacobs et al. (1985) Nature 313:806-810; Lin et al. (1985) Proc. Natl. Acad. Sci. USA 82:7580; International Publication Number WO 85/02610; and European Patent Publication Number 232,034 B1. In addition, the sequences of the genes encoding native feline, canine and porcine EPO are known and readily available (GenBank Accession Nos.: L10606; L13027; and L10607, respectively), and the sequence of the gene encoding monkey is also known and available (GenBank Accession No.: L10609).

The expression of EPO in the subject in need thereof can be performed by introducing an agent into target cells that increases expression of EPO. The target cells can include cells within the GI tract or other suitable parts of the body. The agent can comprise natural or synthetic EPO nucleic acids that are incorporated into recombinant nucleic acid constructs, typically DNA constructs, capable of introduction into and replication in the cell.

Other agents can also be introduced the target cells to promote EPO expression in a target tissue. For example, agents that increase the transcription of a gene encoding EPO; increase the translation of an mRNA encoding EPO, and/or those that decrease the degradation of an mRNA encoding EPO could be used to increase EPO levels. Increasing the rate of transcription from a gene within a cell can be accomplished by introducing an exogenous promoter upstream of the gene encoding EPO. Enhancer elements, which facilitate expression of a heterologous gene may also be employed.

One method of introducing the agent into a target cell involves using gene therapy. Gene therapy in accordance with the present invention can be used to express EPO or its peptide analog from a target cell in vivo or in vitro. An example of a gene therapy method involves using a vector including a nucleotide encoding EPO or its peptide analog. Examples of vectors that can be used include, for example, viral vectors (such as adenoviruses ('Ad'), adeno-associated viruses (AAV), and retroviruses), liposomes and other lipid-containing complexes, and other macromolecular complexes capable of mediating delivery of a polynucleotide to a target cell. Such a construct can include a replication system and sequences that are capable of transcription and translation of a polypeptide-encoding sequence in a given target cell.

The vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Vectors for use in expressing EPO or its peptide analog in the present invention include viral vectors, lipid based vectors, and other vectors that are capable of delivering nucleotide according to the present invention to the target cells. Viral vectors for use in the invention can also be those that exhibit low toxicity to a target cell and induce production of therapeutically useful quantities of EPO in a tissue-specific manner. One example of a viral vector that can be used for expressing EPO in a target cell is adeno-associated virus (AAV). Such AAV vectors that can be used express EPO or its peptide analog in target cells are described in U.S. Pat. No. 6,325,998, which is herein incorporated by reference. Other vectors including viral and non-viral vectors well known in the art and described above can also be used.

In addition to viral vector-based methods, non-viral methods may also be used to introduce a gene into a target cell. An example of a non-viral gene delivery method according to the invention employs plasmid DNA to introduce a nucleic acid into a cell. Plasmid-based gene delivery methods are known in the art.

The vectors that encode the expression of EPO or its peptide analog can be delivered to the target cell in the form of an injectable preparation containing pharmaceutically acceptable carrier such as saline, for example, as necessary. Other pharmaceutical carriers, formulations and dosages can also be used. The EPO or its peptide analog may be expressed for any suitable length of time including transient expression and stable, long-term expression. In one embodiment, the EPO or its peptide analog will be expressed in therapeutic amounts for a suitable and defined length of time so as to treat and/or prevent gastrointestinal dysfunction, such as intestinal dysmotility.

Additional Definitions

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation).

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

A conservative modification or functional equivalent of a peptide, polypeptide, or protein disclosed in this invention refers to a polypeptide derivative of the peptide, polypeptide, or protein, e.g., a protein having one or more point mutations, insertions, deletions, truncations, a fusion protein, or a combination thereof. It retains substantially the activity to of the parent peptide, polypeptide, or protein (such as those disclosed in this invention). In general, a conservative modification or functional equivalent is at least 60% (e.g., any number between 60% and 100%, inclusive, e.g., 60%, 70%, 75%, 80%, 85%, 90%, 95%, 96%, 97%, 98%, and 99%) identical to a parent (e.g., one of SEQ ID NOs: 1-4). Accordingly, within scope of this invention are hinge regions having one or more point mutations, insertions, deletions, truncations, a fusion protein, or a combination thereof.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder. The terms "prevent," "preventing," "prevention," "prophylactic treatment" and the like refer to reducing the probability of developing a disorder or condition in a subject, who does not have, but is at risk of or susceptible to developing a disorder or condition.

An effective amount refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment. A therapeutically effective amount of an agent for increasing intestinal motility is an amount that will cause, for example, an increase in gastrointestinal transit, as compared to untreated animals.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Examples

Materials and Methods

Animals included wild-type (C7BLK6, (WT)) and those selectively deficient in the expression of the receptor for erythropoietin (EPO-R) on Schwann cells (MPZ Cre+EPO-R−/−, (MPZ)). Animals were divided into six groups (groups 1-3, WT; groups 5-7, (MPZ)). Group 1 underwent sham surgery. Group 2 underwent intestinal manipulation treated with saline as a control for Group 3 animals, which underwent intestinal manipulation treated with EPO.

Animals

Male C57BL/6 mice weighing 20-25 g (Jackson laboratory) between 6-8 week old were housed in a pathogen-free, *Helicobacter* negative facility that was accredited by the American Association for Accreditation of Laboratory Animal Care and which complied with the requirements of humane animal care as stipulated by the United States Department of Agriculture and the Department of Health and Human Services. The research protocol was approved by the Institutional Animal Use and Care Committee of the University of Rochester. The animals were maintained on a 12-h light/dark cycle and provided with commercially available chow and tap water ad libitum.

Animal Model of POI

The animals were randomly subjected either to unoperated, Intestinal manipulation (IM) with EPO treatment or sham saline treatment (N=5 each group and each experiment). The small bowel of the animals was subjected to surgical manipulation as described by in Vioz T O et al., Functional assessment of intestinal motility and gut wall inflammation in Rodents. *J Vis Exp.* 2012 Sep. 11; (67). pii: 4086. doi: 10.3791/4086. Unoperated and operated vehicle-injected animals served as corresponding controls. In brief, the animals were anesthetized with isoflurane inhalation and a midline incision was made into the peritoneal cavity. The small bowel was eventrated onto moist gauze and the entire small bowel was lightly manipulated between two moist cotton applicators. After manipulation, the laparotomy was closed by using a double-layer running suture. The bowel manipulation procedure caused no mesenteric vascular bleeding or mortality. Immediately postoperatively, mice received 100 µl of EPO intraperitoneal injection at 5000 IU/kg. Control mice received the respective amount of normal saline vehicle. The animals recovered quickly from surgery and generally began to eat and drink within 2 hours. The animal were sacrificed 24 hours after manipulation, and the intestine was used for in vivo gastrointestinal transit studies, histochemistry and immunohistochemistry.

Functional Studies

Gastrointestinal transit was measured in controls and manipulated animals at 24 h postoperatively by evaluating the intestinal distribution of fluorescent FITC-labeled dextran (Molecular Probes, Eugene, Oreg.). The animals were given FITC-labeled dextran (10 µl of 25 mg/ml stock solution) via gavage. Ninety minutes after administration, the entire GI tract (stomach to colon) was removed. The small bowel was divided into 10 equal parts, and the colon was divided into three equal parts. Supernatants of the intestinal chyme were fluorometrically assayed for the FITC-D concentration. The gastrointestinal distribution was analyzed by calculating the geometric center (GC) using the following formula; GC=R (% of total fluorescent signal per segment number)/100.

To assess GI transit, 10 1L of a liquid non-absorbable fluorescein isothiocyanate-labeled dextran (FITC-dextran, 70 000 Da; Invitrogen, Merelbeke, Belgium) was administered by oral gavage to fasted animals. Ninety min after oral gavage, the animals were sacrificed by $CO_2$ overdose and the contents of stomach, small bowel (divided in 10 segments of equal length), caecum, and colon (divided in three segments of equal length) were collected and the amount of FITC in each bowel segment was quantified using a spectrofluorimeter (Ascent; Labsystem Inc., Ghent, Belgium) at 488 nm. The distribution of the fluorescent dextran along the GI tract was determined by calculating the geometric center (GC): Σ (percent of total fluorescent signal in each segment 9 the segment number)/100 for quantitative comparison among experimental groups.

Whole Mount Preparation and MPO Staining

Segments of jejunum were 150% stretched and fixed with 100% ethanol for 10 minutes. Mucosa and submucosa were removed and the remaining full-thickness sheets of ME were stained with Hanker Yates reagent (Sigma-Aldrich, Diegem, Belgium) for 10 min. Nine images of myeloperoxidase (MPO) positive cells in the ME were taken using a microscope (BX 41; Olympus, Aartselaar, Belgium) connected to a camera (XM10; Olympus). The number of MPO-positive cells was counted by an observer blind to the experimental conditions in 5 randomly chosen representative low-power magnification fields (acquired with the 109 objective, 668.4 lm 9 891.2 lm).

Immunohistochemistry Staining

For immunohistochemical quantification of infiltrating monocytes, Mid jejunal segments were fixed in 4% Paraformaldehyde, paraffin blocks were made, microtome used to create sections. Whole mounts were incubated with a rat monoclonal anti-mouse F4/80 antibody conjugated with TrueBlue Chromogen. Immunocytes were counted in five randomly chosen areas in each specimen at a magnification of 200×.

Solutions and Statistics

A standard Krebs Ringers buffer (KRB) was used. Results were presented as means±standard error of the mean (SEM). EZAnalyze ANOVA was used to perform the F-test and Bonferroni post hoc group comparisons where appropriate. P values<0.05 were considered significant.

Results

Functional Improvement of Motility after EPO Administration

Figure 1B:
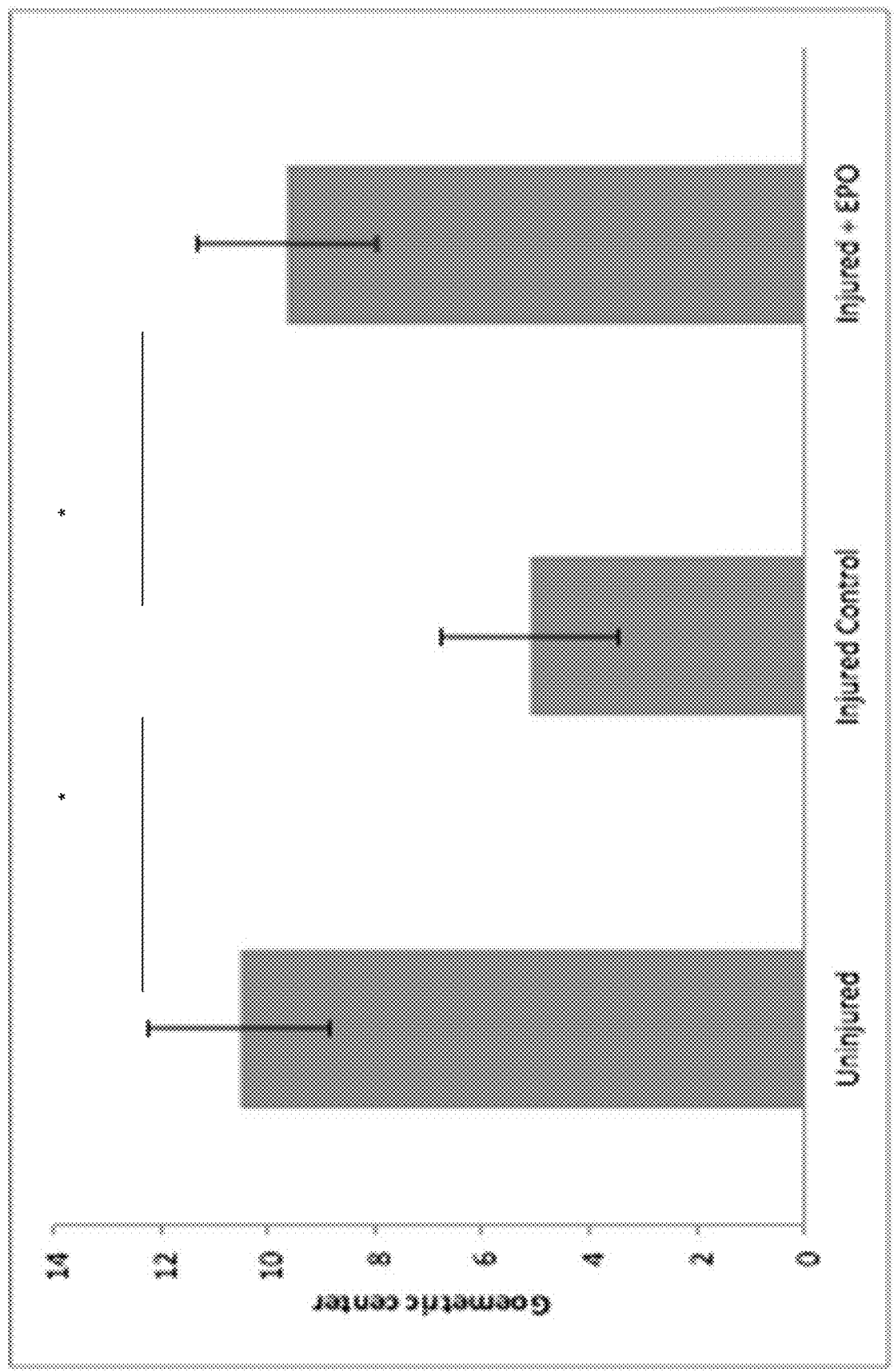
FIG. 1B is a diagram showing geometric center of gastrointestinal transit. Calculated, weighted geometric center of fluorescence transit through the gut. Distributions show significant differences between injured control and injured treated with EPO and between injured control and uninjured (p<0.05, F Statistic=16.61, Prob F>0.0010). No significant difference was found between EPO treated and uninjured.

First, it was aimed to test the hypothesis that EPO treatment would have a significant effect on the natural course of dysmotility in a standard model of injury in a wild-type rodent. Animals underwent laporotomy and intestinal manipulation 24 hours before testing with a dextran bolus. The bolus, not absorbed in the gut was allowed to proceed through the gastrointestinal tract for 60 minutes. In the injured animals, this significantly shifted the location of the dextran bolus along the GI-tract toward earlier segments (FIG. 1A, red line injured vs blue line uninjured). This standard shift in transit was the result of ileus which allowed less transit in the minutes between bolus and sacrifice. The uninjured animals processed and moved the bolus faster and therefore showed a geometric center further along the GI tract than the injured counterparts treated with control saline injection. In contrast to the injured-control animals, the EPO treatment shifted the transit toward later segments in the GI tract. This shift was significant in that EPO treated animals were statistically indistinguishable from uninjured animals (FIG. 1B).

EPO Mediated Effects on Motility were Absent in Animals Selectively Deficient in Receptors for EPO on Glia Animals selectively deficient in the expression of the receptor for EPO in glial cells were generated. These animals were functionally normal and subjected to characterization (with various tissue based analyses). As a preliminary test of the effect of this deficiency on intestinal motility intestinal manipulation was performed in these animals with and without EPO treatment and compared gastrointestinal transit to both uninjured, genetically identical animals.

Figure 2A:
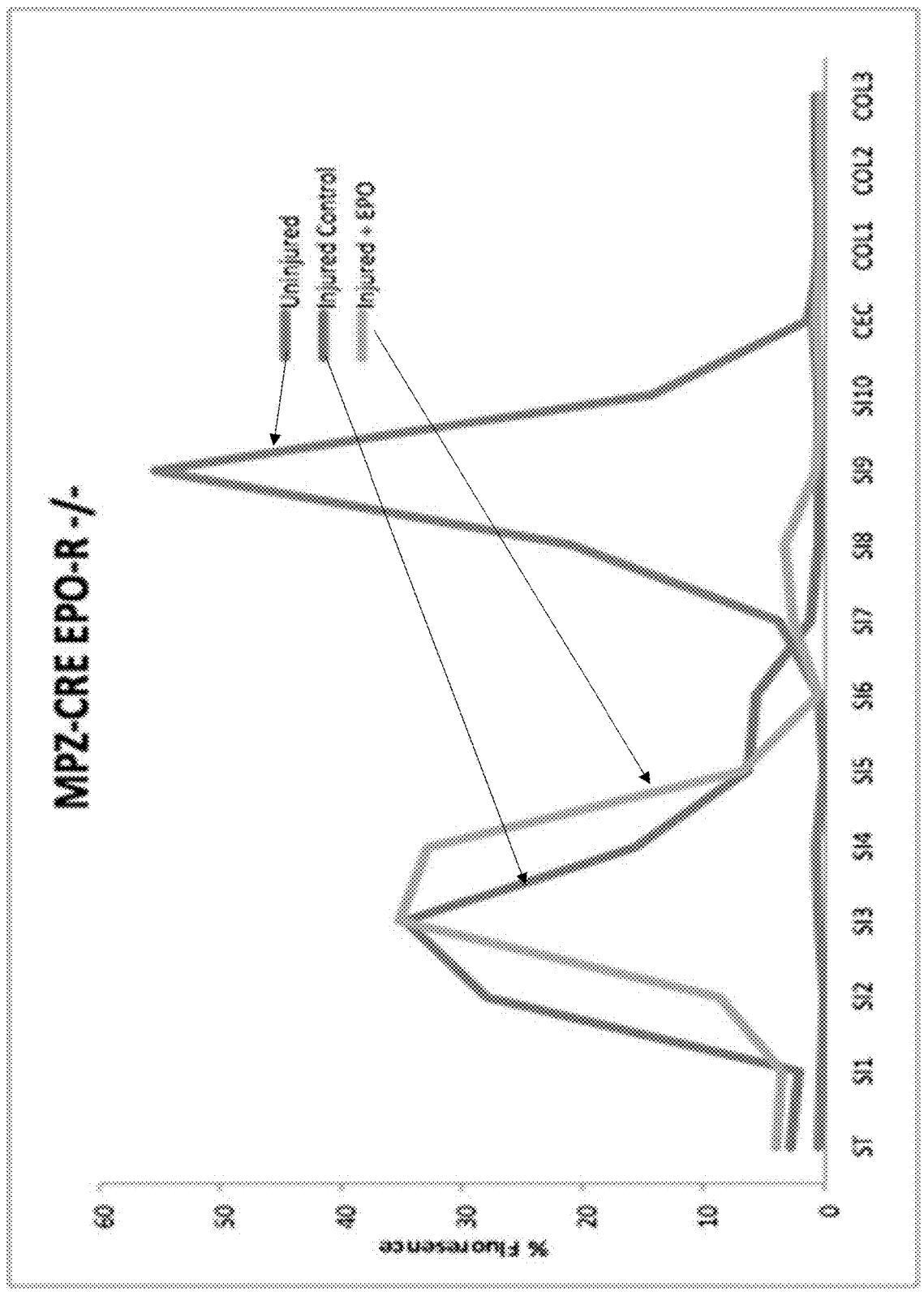
FIG. 2A is a diagram showing that animals selectively deficient in the expression of the receptor for erythropoietin on glial cells did not show a response to EPO treatment after intestinal manipulation. Injured control animals did not significantly differ from EPO treated counterparts after intestinal manipulation but both treated and untreated differed from uninjured animals.
Figure 2B:
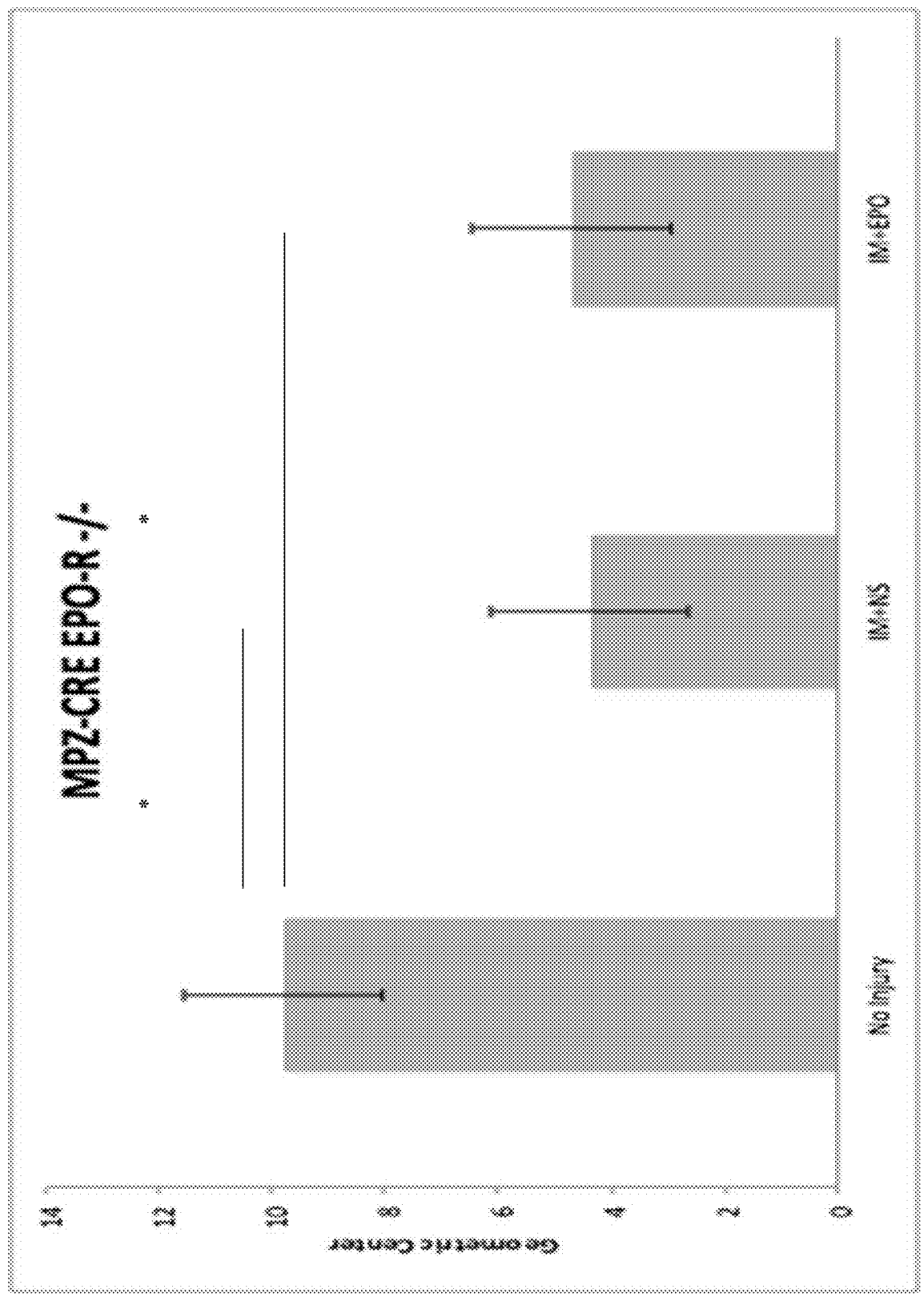
FIG. 2B is a diagram showing that geometric center of gastrointestinal transit in animals deficient in EPO receptor expression on glial cells did not change with EPO treatment. Calculated, weighted geometric center of fluorescence transit through the gut. Distributions showed no significant differences between injured control and injured treated with EPO (p>0.05).

Animals without injury did not differ significantly from their wild-type counterparts in terms of gastrointestinal transit (compare FIGS. 1 and 2), but EPO treatment in animals without EPO-R expression on glial cells did not show significant improvement with EPO treatment compared with injured control counterparts (FIGS. 2A and B).

Preliminary Tissue Based Analyses

Figures 3A, 3B, 3C, 3D, 3E, 3F:
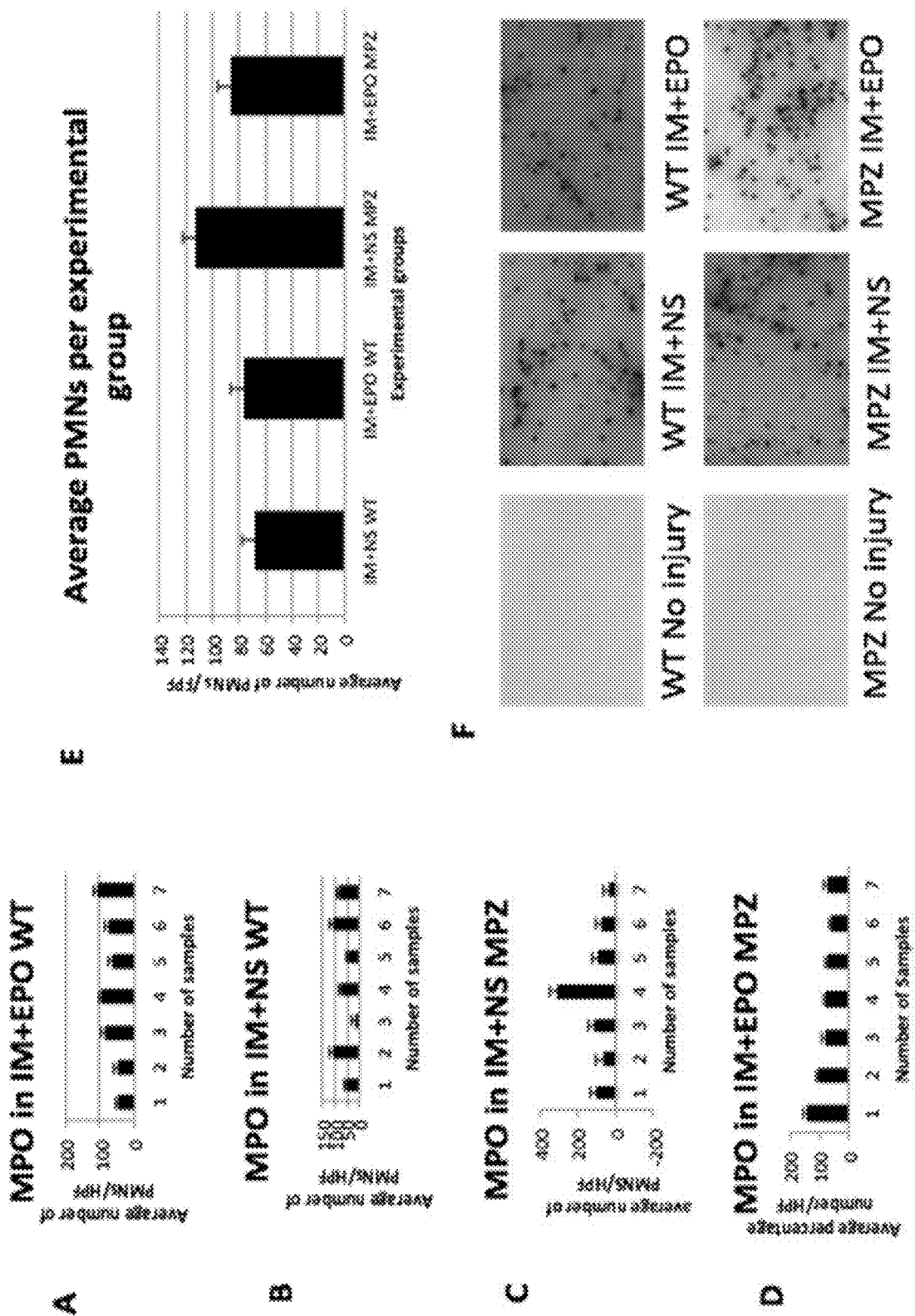
FIGS. 3A, 3B, 3C, 3D, 3E, and 3F are a set of photographs showing that injury induced inflammatory changes as gauged by myeloperoxidase activity without significant effect of EPO in either wild-type mice or those deficient in the expression of the receptor for EPO on glial cells. Panel A, average number of polymorphonuclear leukocytes per high power field in individual wild-type, EPO treated mice; panel B wild-type, untreated mice; panel C, untreated receptor deficient mice; panel D, treated receptor deficient mice. Compared with uninjured, panel F, mice showed no myeloperoxidase staining in either mouse strain. No significant differences were found in the average number of PMNs between treated and untreated injured groups (n=7, p>05 for all individual group comparisons).

Mucosal samples from all mice were analyzed for the presence of inflammatory markers based on previous studies. Myeloperoxidase (MPO) staining was used to stain for polymorphonuclear leukocytes (PMNs) in intestinal tissue and no PMNs were found in uninjured intestine (FIG. 3). Although injury significantly increased the number of PMNs in both wild-type and glial-cell-EPO-receptor deficient mice, no significant differences were found between these groups (n=7 per group).

Similar results were found with staining for glial fibrillar acid protein (GFAP), a known marker of activated glial cells (data not shown, n=3 per group). Macrophage stains for activity were also examined.

The primary tissue effect of EPO in dysmotility remains unknown. Indeed, several motility agents are currently used in humans without well-defined mechanistic detail. Inventors' data from animals selectively deficient in the expression of the receptor for EPO in Schwann cells implicates glial cells in the effect of EPO on gut dysmotility. Nonetheless, additional studies are ongoing regarding the mechanism of action of this erythropoietic hormone on dysmotility.

EPO mediated effects on dysmotility may have origins in a variety of tissue types. The gut, contains muscle tissue responsible for propelling boluses of food forward and mucosae for secretion and reabsorbtion. There is also a vast network of innervation, support cells, glia, vessels among other tissues. Nearly every cell type in this system has been shown to express the receptor for EPO. The inventors' work is but a first venture into defining single tissue types and cell types in the pathophysiologic processes which may be amenable to EPO administration.

The results shown above indicate that EPO is an attractive agent for use in the assessment of and treatment of dysmotility as it is already used in humans for other indications and has a favorable side-effect profile. Several indications can be envisioned for at least a trial of EPO as a promotability agent. It should be noted that the treatment with EPO in this model is temporally close to the point of assessment, providing a partial answer to the question of whether EPO can act effectively as a diagnostic for dysmotility. If patients with occult dysmotility respond to exogenous EPO treatment with improved motility, then EPO treatment can serve as an adequate diagnostic of the extent of dysmotility. The functional results, coupled with the availability and favorable profile of this agent will allow early transition to human clinical trials.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method for increasing intestinal motility in a mammal that has gastrointestinal dysmotility and does not have anemia, the method comprising administering to the mammal an effective amount of erythropoietin (EPO) or an analog thereof, wherein the analog comprises the sequence of SEQ ID NO: 1, SEQ ID NO: 2, SEQ ID NO: 3 or SEQ ID NO:4.

2. The method of claim 1, wherein the subject mammal is suffering from a condition selected from the group consisting of an intestinal injury, an abdominal trauma, an intestinal inflammatory condition, an intestinal infection, slow transit constipation, post-operative ileus, a neurodegenerative injury, a neurotraumatic injury, a congenital problem, and a malnutrition-malabsorption problem.

3. The method of claim 2, wherein the malnutrition-malabsorption problem is caused by one or more selected from the group consisting of an intestinal injury, an abdominal trauma, an intestinal inflammatory condition, an intestinal infection, constipation, post-operative ileus, a neurodegenerative injury, a neurotraumatic injury, a congenital problem, Gaucher disease, refeeding syndrome, extremely low birth weight infants, cancer cachexia, infection, cancer, spinal cord dysfunction, spinal dysraphism, bifida, tumor, central nervous system dysfunction, peripheral neuropathy, removal part of the gastrointestinal tract, hemorrhage, liver dysfunction, celiac disease, cystic fibrosis, muscular dystrophies, and cerebral palsy.

4. The method of claim 2, wherein the congenital problem is selected from the group consisting of Gastroschisis, omphalocele, aganglionic megacolon, Hirschprung's disease, chronic intestinal pseudo-obstruction, small left colon syndrome, anorectal anomalies, esophageal dysplasia and atresias, ectopic anus, congenital hernias, and internal anal sphincter achalasia.

5. The method of claim 2, wherein the condition is an intestinal inflammatory condition.

6. The method of claim 2, wherein the constipation is caused by opiate use.

7. The method of claim 1, wherein the mammal does not have acute uremia due to kidney failure.

8. The method of claim 1, wherein the EPO or analog is administered as a conjugate.

9. The method of claim 8, wherein the conjugate is a PEGylated erythropoietin or analog thereof.

10. The method of claim 1, wherein the EPO or the analog thereof is administered at 100 to 1,000 U/kg.

11. The method of claim 10, wherein the EPO or the analog thereof is administered at 200-500 U/Kg.

12. The method of claim 11, wherein the EPO or the analog thereof is administered at 250-350 U/kg.

13. The method of claim 1, wherein the mammal is a human.

14. The method of claim 1, wherein the mammal is a non-human mammal.

15. The method of claim 1, wherein the EPO or the analog is administered orally.

16. The method of claim 1, wherein the EPO or the analog is administered by insertion, implantation or injection into the mammal.

17. The method of claim 1, wherein the EPO or the analog is administered by subcutaneous injection or intravenous injection.

18. The method of claim 1, comprising administering erythropoietin or the analog to the mammal over a treatment period of at least 24 hours.

19. The method of claim 18, comprising administering erythropoietin or the analog to the mammal over a treatment period of 24 hours to years.

* * * * *